United States Patent
Haberland et al.

(10) Patent No.: US 8,608,827 B2
(45) Date of Patent: Dec. 17, 2013

(54) PORTABLE AND STATIONARY OXYGEN CONCENTRATOR SYSTEM

(75) Inventors: Bernhard Lewis Haberland, Palm City, FL (US); Joseph Thomas Dolenski, Kennesaw, GA (US); Jeremy Blair, Atlanta, GA (US); Donald Kenneth Griffin, Marietta, GA (US); Marvin Norman Zeigler, Woodstock, GA (US); Gerry Dean Richardson, Kennesaw, GA (US)

(73) Assignee: Koninklijke Philips N.V., Eindhoven (NL)

( * ) Notice: Subject to any disclaimer, the term of this patent is extended or adjusted under 35 U.S.C. 154(b) by 239 days.

(21) Appl. No.: 13/132,482

(22) PCT Filed: Nov. 21, 2009

(86) PCT No.: PCT/IB2009/055262
§ 371 (c)(1),
(2), (4) Date: Jun. 2, 2011

(87) PCT Pub. No.: WO2010/073140
PCT Pub. Date: Jul. 1, 2010

(65) Prior Publication Data
US 2011/0232483 A1 Sep. 29, 2011

Related U.S. Application Data

(60) Provisional application No. 61/139,745, filed on Dec. 22, 2008.

(51) Int. Cl.
*B01D 53/047* (2006.01)

(52) U.S. Cl.
USPC .......... 95/23; 95/96; 96/109; 55/356; 55/357; 128/204.18; 128/204.21; 128/204.25

(58) Field of Classification Search
USPC ............. 128/204.18, 204.21, 204.25; 55/356, 55/357; 95/23, 96; 96/109
See application file for complete search history.

(56) References Cited

U.S. PATENT DOCUMENTS

| | | | | |
|---|---|---|---|---|
| 5,713,984 | A | * | 2/1998 | Monnot et al. ................... 95/100 |
| 6,095,138 | A | * | 8/2000 | Hognelid et al. ........ 128/204.18 |
| 6,346,139 | B1 | | 2/2002 | Czabala |
| 6,651,658 | B1 | * | 11/2003 | Hill et al. ................. 128/204.23 |
| 6,916,358 | B2 | * | 7/2005 | Nakamura et al. ................ 95/96 |
| 2002/0096174 | A1 | * | 7/2002 | Hill et al. ................. 128/205.11 |
| 2003/0051730 | A1 | * | 3/2003 | Thuener .................. 128/204.26 |
| 2005/0160905 | A1 | * | 7/2005 | Whitley et al. .................... 95/90 |
| 2005/0161043 | A1 | * | 7/2005 | Whitley et al. .......... 128/205.18 |
| 2006/0174877 | A1 | * | 8/2006 | Jagger et al. ............. 128/201.21 |
| 2008/0047426 | A1 | * | 2/2008 | Dolensky .......................... 95/22 |
| 2008/0047435 | A1 | | 2/2008 | Dolensky |
| 2008/0202508 | A1 | * | 8/2008 | McClain et al. ......... 128/201.21 |
| 2012/0055340 | A1 | * | 3/2012 | Wilkinson et al. .............. 96/115 |

FOREIGN PATENT DOCUMENTS

EP 1568391 A1 8/2005

* cited by examiner

*Primary Examiner* — Christopher P Jones
(74) *Attorney, Agent, or Firm* — Michael W. Haas

(57) ABSTRACT

An oxygen generator includes a stationary unit and a portable unit. The portable unit includes a compressor, molecular sieves, controllable valves and an enriched gas storage chamber. The stationary unit includes a compressor having a greater capacity than a capacity of the portable compressor.

19 Claims, 2 Drawing Sheets

PORTABLE AND STATIONARY OXYGEN CONCENTRATOR SYSTEM

CROSS-REFERENCE TO RELATED APPLICATIONS

This patent application claims the priority benefit under 35 U.S.C. §119(e) of U.S. Provisional Application No. 61/139,745 filed on Dec. 22, 2008, the contents of which are herein incorporated by reference.

BACKGROUND OF THE INVENTION

1. Field of the Invention

The invention relates generally to systems for concentrating oxygen from ambient air, and, more particularly, to a system including a portable component and a stationary component.

2. Description of the Related Art

For patients having a need for home based oxygen therapy, compressed gas tank deliveries can be inconvenient and expensive. Oxygen tanks provide a limited supply and require a great deal of storage space within the home, particularly where a patient's usage is high. As a result, there is a need for systems for generating oxygen in the home, such that an essentially unlimited supply of oxygen can be provided.

Home oxygen concentrators, typically employing a pressure swing adsorption system to separate oxygen from air, are capable of providing continuous oxygen delivery in the range of about 1-6 liters per minute. In general, for trips outside the home, patients using oxygen concentrators carry oxygen tanks that are delivered by an outside vendor, supplemental to the concentrator.

As an alternative to separate tanks, portable concentration systems have been developed to provide ambulatory patients with oxygen while away from the stationary system. In general, such portable systems have had a relatively low capacity due to weight and size constraints. One solution to this problem has been described in U.S. Pat. No. 6,346,139, the contents of which are incorporated herein by reference in its entirety.

SUMMARY OF THE INVENTION

One aspect of the invention relates to an oxygen generator including a first compressor, configured and arranged to provide a flow of pressurized air, a first molecular sieve, coupled to the compressor to receive the flow of pressurized air and to produce a flow of oxygen enriched gas, a second molecular sieve, coupled to the compressor to receive the flow of pressurized air and to produce a flow of oxygen enriched gas, a control valve, configured and arranged to control the flow of pressurized air such that it is alternately provided to the first and second molecular sieves, a product container, coupled to the molecular sieves to receive the flow of oxygen enriched gas, an outlet valve, coupled to the product container and configured and arranged to regulate an output flow of oxygen enriched gas to a user, a purge line, coupling the first and second molecular sieves and configured and arranged to control a flow of purge gas therebetween during a purge cycle, and a coupler, constructed and arranged to accept a gas line connection from a second compressor that is external to the portable oxygen generator and has a larger capacity than the first compressor, such that, when connected, the molecular sieves receive the flow of pressurized air from the second compressor, and to, in response to acceptance of the gas line, signal a controller to turn off the first compressor.

Another aspect of the invention relates to a oxygen generator including a first compressor, configured and arranged to provide a flow of pressurized air, a first molecular sieve, coupled to the compressor to receive the flow of pressurized air and to produce a flow of oxygen enriched gas, a second molecular sieve, coupled to the compressor to receive the flow of pressurized air and to produce a flow of oxygen enriched gas, a control valve, configured and arranged to control the flow of pressurized air such that it is alternately provided to the first and second molecular sieves, a product container, coupled to the molecular sieves to receive the flow of oxygen enriched gas, an outlet valve, coupled to the product container and configured and arranged to regulate an output flow of oxygen enriched gas to a user, a purge line, coupling the first and second molecular sieves and configured and arranged to control a flow of purge gas therebetween during a purge cycle, the purge line coupling output sides of the molecular sieves such that the purge gas comprises oxygen enriched gas, and a coupler, configured and arranged to accept a gas line connection from a second compressor that is external to the portable oxygen generator and has a larger capacity than the first compressor.

Another aspect of the invention relates to a method of providing oxygen enriched gas to an end user at a range of flow rates including compressing ambient air at a first flow rate using a first compressor, controllably supplying the compressed air to first and second molecular sieves, storing oxygen enriched product gas from the molecular sieves, controllably providing the oxygen enriched product gas to a user, coupling a second compressor to the molecular sieves to supply compressed air to the molecular sieves at a second flow rate higher than the first flow rate, and in response to the coupling of the second compressor, turning off the first compressor.

Still another aspect of the invention relates to an oxygen generator including a compressor, configured and arranged to provide a flow of pressurized air, a first molecular sieve, coupled to the compressor to receive the flow of pressurized air and to produce a flow of oxygen enriched gas, a second molecular sieve, coupled to the compressor to receive the flow of pressurized air and to produce a flow of oxygen enriched gas, a control valve, configured and arranged to control the flow of pressurized air such that it is alternately provided to the first and second molecular sieves, a product container, coupled to the molecular sieves to receive the flow of oxygen enriched gas, an outlet valve, coupled to the product container and configured and arranged to regulate an output flow of oxygen enriched gas to an end user, a purge line, coupling the first and second molecular sieves and configured and arranged to control a flow of purge gas therebetween during a purge cycle, and a controllable purge line valve that is configured and arranged to selectively control an amount of flow during the purge cycle and is operable to select between at least two purge orifices having different diameters to control the amount of flow during the purge cycle.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE EXEMPLARY EMBODIMENTS

Figure 1:
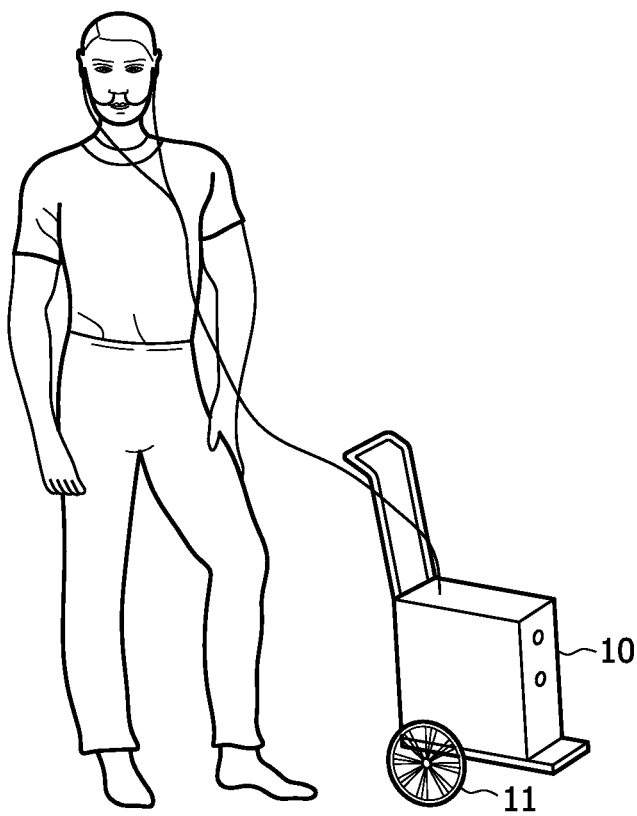
FIG. 1 illustrates a portable oxygen concentrating device for use in the present invention.
Figure 2:
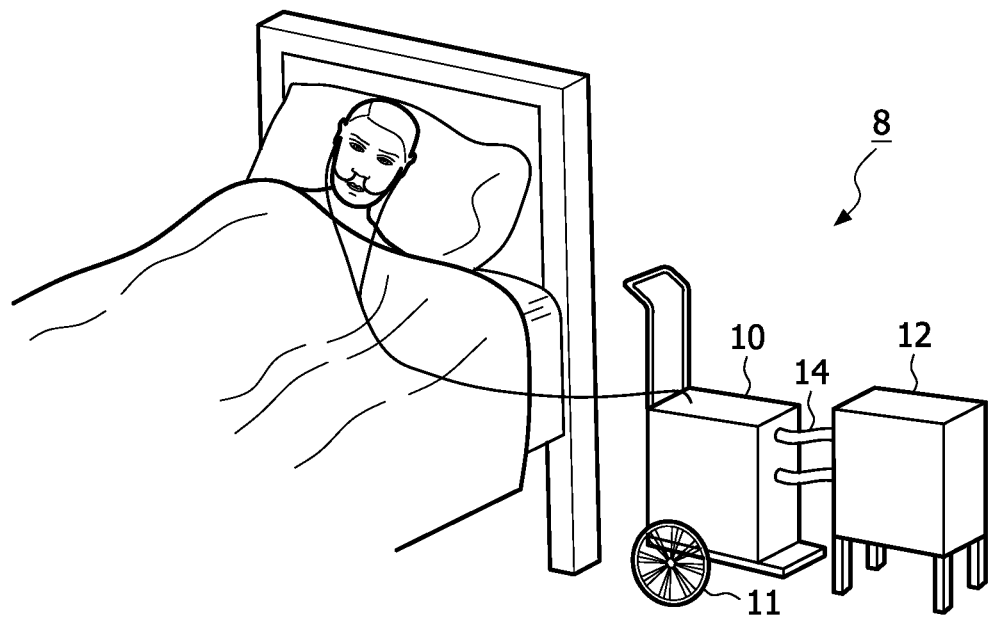
FIG. 2 illustrates a portable oxygen concentrating device being used in conjunction with a stationary portion.

As shown in FIGS. 1 and 2, a dual mode oxygen generator 8 may be used to provide oxygen to a patient in either a portable or stationary mode. Note that in a stationary mode, a sufficiently long cannula would allow a patient to be ambulatory within a limited area (throughout a home, for example) while leaving the generator in one place. The dual mode generator 8 includes a portable oxygen concentrating device 10 that provides the patient with a flow of oxygen concentrated from ambient air. In an embodiment, the portable portion of the system is mounted on a wheeled cart 11. In alternate embodiments, the portable portion may be shoulder slung or in a backpack style arrangement, for example.

In stationary mode, portable oxygen concentrating device 10 is operatively associated with a stationary portion 12 as shown in FIG. 2. Details of the interconnections are described in greater detail below.

Figure 3:
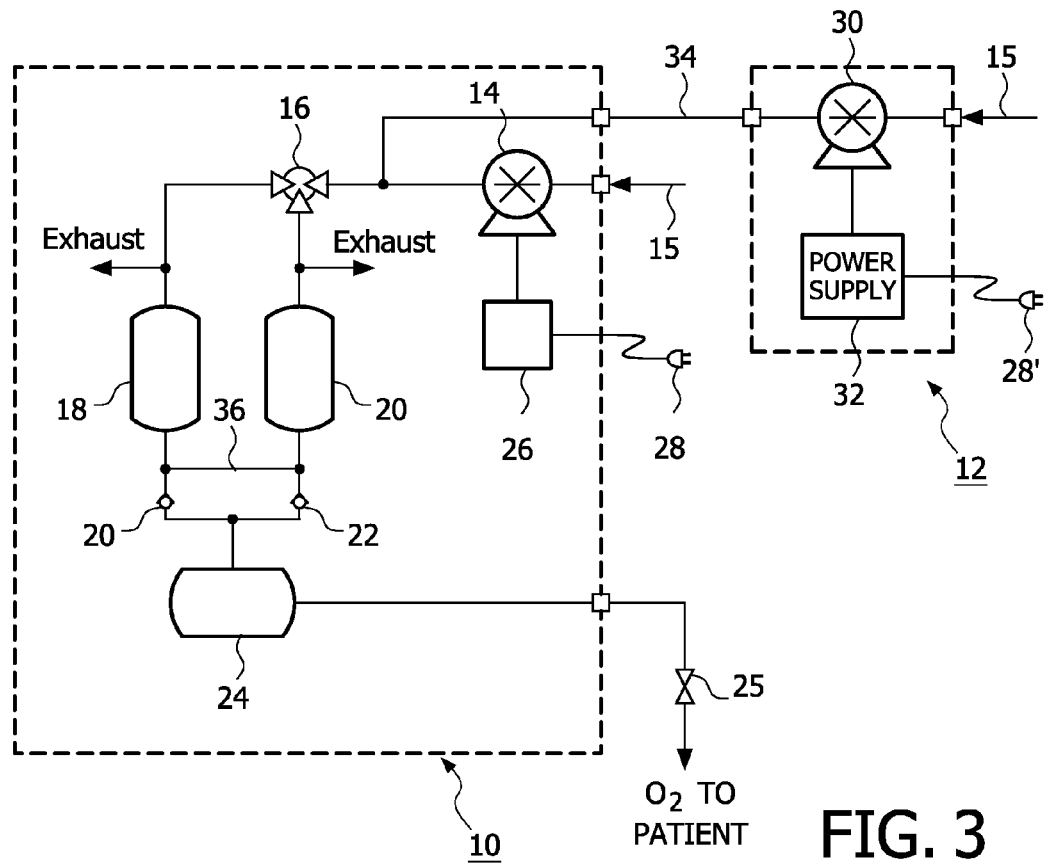
FIG. 3 schematically illustrates an oxygen generating system in accordance with an embodiment of the invention.

FIG. 3 schematically illustrates an embodiment of portable oxygen concentrating device 10. Device 10 operates by a pressure swing adsorption (PSA) method. Portable device 10 includes a compressor 14 that compresses ambient air 15, and provides it to a valve 16 that controls flow into a pair of molecular sieves 18, 20. In an embodiment, ambient air 15 first passes through an air filter (not shown) to remove particulate matter prior to compression and oxygen concentration. In operation, valve 16 alternately provides the compressed air to the sieves, each of which includes a nitrogen binding material such as zeolite. As the compressed air passes through the zeolite, nitrogen is extracted, leaving an oxygen-enriched gas. While one of the sieves is receiving compressed air for nitrogen extraction in a concentration cycle, the other is operating in a regenerating mode in which bound nitrogen is released, preparing that sieve for a next concentration cycle.

Oxygen-enriched air passes through check valves 20, 22 to reach a product tank 24 where it is stored. From product tank 24, oxygen-enriched air may be provided directly to a patient via valve 25, which may be, for example, a proportional valve, controllable to vary the output flow rate of the system. The output line, in addition to valve 25, may further include a differential pressure transducer and/or oxygen purity sensor to allow for additional control and/or monitoring of functionality.

Prior to delivery to the patient, the gas may be passed through a distilled water bubbler to replace/increase humidity, thereby increasing patient comfort. As necessary or desirable, the patient delivery line may include a connector for attaching a breathing mask or a nasal cannula. Furthermore, both the exit path for enriched gas and the intake path for ambient air may include a filter to reduce particulates in the gas stream.

Compressor 14 is powered by a power supply 26. In an embodiment, the power supply 26 includes a battery pack (not shown) and recharging hardware that can draw power via an electrical connector 28. Once charged, the device draws on the battery pack and the connector 28 can be removed or stowed, as desired.

In FIG. 2, portable device 10 and stationary device 12 are shown as separate units. It should be understood that stationary device 12 may be configured as a docking station that receives a portion or all of the physical housing of the portable device 10 similar to a laptop computer docking station.

In general, a compressor 14 that is suitably portable does not have sufficient capacity to provide high levels of oxygen flow. This is due to, for example, size and weight as well as energy consumption requirements. With appropriate selection of sieve size and materials, the limiting factor for oxygen output of the portable system is not the sieves, but rather the compressor's capacity. Thus, in order to supply oxygen at a high rate (e.g., 5 l/m or more) stationary device 12 includes a compressor 30 that has a higher capacity than does portable compressor 12.

Power is delivered via a power supply 32 that is connectable to an outlet via electrical connector 28'. Stationary compressor 30 may be larger, heavier and consume more power than portable compressor 12 because it does not generally have to be moved by the patient and can draw on the home's AC electrical system rather than portable battery packs.

By way of example, a portable compressor with a capacity of 12-14 l/m is capable of producing about 1 l/m of enriched product gas using an air-side balance approach. Using the oxygen-side balance approach in accordance with a below-described embodiment, 1 l/m of product gas may be produced using an input of about 10-11 l/m. In order to provide a 2 l/m output, the portable compressor may therefore be designed to produce 20-28 l/m (20-22 l/m for the oxygen-side balance embodiment). In comparison, in order to provide a 5 l/m output, the stationary compressor may have a capacity of 50-70 l/m.

As a result of this arrangement, complete system 10, 12, when working together is able to supply a higher flow of oxygen to the patient than could portable system 10 alone. Stationary system 12, which has no expensive oxygen generating components such as the molecular sieves, can be manufactured inexpensively.

Connector 34 removably connects portable device 10 to stationary device 12. In an embodiment, connector 34 is a quick connect gas line that provides for pressurized air flow from stationary compressor 30 to the portable device 10. Within portable device 10, flow from connector 34 is provided as an input to control valve 16 and supplied therefrom to molecular sieves 18, 20 for purification.

In an embodiment, upon connection of portable device 10 to stationary device 12, portable compressor 14 is shut off in favor of stationary compressor 30. While such shut off may be implemented manually, an automatic shut off is a useful approach.

Automatic shutoff can be achieved in a number of ways. An electrical sensor (not shown) may be configured and arranged to sense the presence of the connector 34 and to provide a control signal to compressor 14. In an alternate approach, a pressure sensor, for example positioned in line with connector 34 in portable device 10, could be used to detect pressurized air from compressor 30 and to provide a control signal to turn off compressor 14. Other approaches to shutoff will be apparent to the skilled artisan in view of the foregoing description.

In an embodiment, portable compressor 14 may remain on when the two devices are connected, and work in conjunction with stationary compressor 30. In this embodiment, stationary compressor 30 may have a correspondingly reduced output capacity such that the two compressors together have an output capacity sufficient to meet the patient's need. Making reference to the above example in which the portable compressor has an output of 20-28 l/m and the total requirement is 5 l/m of product gas, the stationary compressor may have an output of 50-70 l/m minus 20-28 l/m, or somewhere in the range of about 22-50 l/m. That is, if the portable compressor is capable of an output of 2 l/m and the total requirement is 5 l/m, the ratio of capacity of the portable to the stationary should be about 2:3.

A purge/regeneration line 36 is provided between the outputs of the sieves 18 and 20. The arrangement as shown is what is referred to above as an oxygen-side balance. Alternately, and not shown, the device may make use of an air-side balancing approach, in which regeneration line 36 would be on an input side of the sieves rather than the output side as shown in FIGS. 3 and 4.

Figure 4:
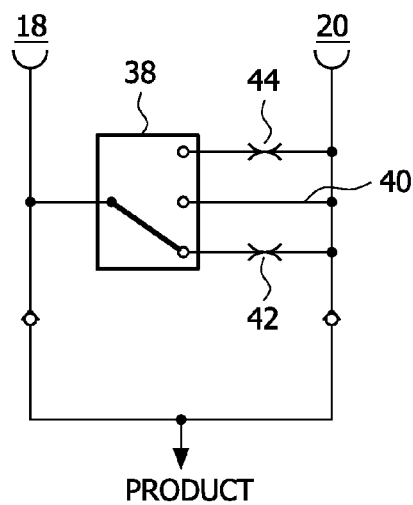
FIG. 4 is a schematic illustration of a portion of a circuit for controlling an oxygen generating system.

In an embodiment, illustrated in FIG. 4, regeneration line 36 includes a controllable valve 38 that allows for additional control of the purging flow between the sieves. In the embodiment of FIG. 4, controllable valve 38 is configured and arranged to select among three different pathways, a balance pathway 40 and two different purge pathways, 42, 44.

The balance pathway 40 allows regeneration line 36 to divert a portion of the oxygen enriched gas flow from the sieve currently in an operational mode to the sieve which is in a regeneration mode to trigger the release of bound nitrogen, thereby regenerating the nitrogen binding substrate.

The other two pathways include respective orifices, 42, 44 and are used for the purge cycle. The orifices have respective different sizes, which alters a flow rate through the system during purge. One result is that a degree of control can be exercised over an amount of oxygen used in the purging process. In an embodiment, an amount of oxygen used is selected in response to a flow rate of compressed air through the portable system 10. The larger orifice is used for higher flow settings while the smaller orifice is used for lower flow settings. As an example, the smaller orifice may be about 20 mils while the larger orifice may be about 30-35 mils in diameter.

As will be appreciated, where there is a wide range of flow rates, it may be useful to include more than two orifices, for example one for very low flows, one for moderate flows and one for high flow rates. Alternately, a single purge orifice having a variable diameter may be useful, though for production cost reasons, it may not be as practical a solution. In general, selecting purge orifice diameter based on flow rates tends to provide improved efficiency, and therefore a lower power requirement on the system. This can translate to improved battery life in a portable system, or to increased energy efficiency in a stationary system.

Operation of oxygen generator 8 at a wide range of flow rates can result in a wide range of pressures present in the sieve beds. At one extreme, pulsed oxygen delivery at a nominal rate 1 l/m corresponds to a much lower continuous delivery rate, meaning the pressure in the sieves may be quite low. At the other extreme, a continuous delivery of 5 l/m can result in a quite high pressure in the sieves. The larger orifice may therefore allow for a decrease in developed pressure in the sieves during high flow rate operations. Correspondingly, the smaller orifice is used for lower flow settings, and helps to avoid very low pressures, which can reduce the efficiency of the sieves.

In addition to purge control through use of the two different sized orifices, the controller may, for example, hold the purge valve open for varying times, shorter times corresponding to less oxygen used, longer times corresponding to more oxygen used in purging. For the purposes of controlling one or both of purge orifice selection and purge cycle time, one input to a controller for the controllable valve may be a flow meter or another indicator of the flow rate (for example, a flow rate setting of a controller of one of devices 10, 12).

In one example of this approach, 1.75 lb. sieve beds were used to produce a 93% oxygen output at 5 standard liters per minute (slpm). This output was achieved by applying approximately 65 slpm flow of compressed air at the compressor, 4.5 s cycle time and a 1 s purge time using a 0.033" diameter purge orifice.

In an embodiment, when the flow rate is high, a larger amount of oxygen is used for purging. Conversely, when the flow rate is low, a smaller amount of oxygen is used for purging. As a larger amount of oxygen is used in purge, an efficiency of the sieves 18, 20 generally improves, optimizing the system. The oxygen side balancing of the PSA system means that for high flow rates, a relatively high rate of oxygen can be delivered to the patient.

In general, higher flow rates will correspond to situations in which stationary compressor 30 is connected. The additional efficiency of the sieves, combined with the greater flow enabled by high capacity compressor 30 more than compensates for the loss of an additional portion of the generated oxygen to the purge process. Thus, in the connected configuration, when running on the more powerful stationary compressor 30, oxygen output of the system 8 is expected to be maximized.

As described above, in an embodiment, the portable device 10 docks with stationary device 12. Upon docking, the fluid connection is made between the two devices. At the same time, electrical connection may be made to allow for recharging of the power supply 26 of portable device 10. The present invention contemplate using any one of a variety of different techniques to physically join or dock the portable device with the stationary device. For example, the stationary unit can be configured with a receiving terminal or docking station shaped to match a corresponding portion of the portable device to allow the two devices to mate together by simply placing the portable device in the "docking station" of the stationary device.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A portable oxygen generator, comprising:
   a first compressor, arranged to provide a flow of pressurized air;
   a first molecular sieve, that receives the flow of pressurized air and produces a flow of oxygen enriched gas;
   a second molecular sieve, that receives the flow of pressurized air and produces a flow of oxygen enriched gas;
   a control valve that controls the flow of pressurized air such that it is selectively provided to the first and second molecular sieves;
   a product container, that receives the flow of oxygen enriched gas;

an outlet valve, arranged to regulate an output flow of oxygen enriched gas to a user;

a purge line, in fluid communication with the first and second molecular sieves and that includes a controllable purge line valve that controls a flow of purge gas between the first and second molecular sieves during a purge cycle, wherein the controllable purge line valve is operable to select between at least two purge orifices having different diameters to control the amount of flow of the purge gas during the purge cycle;

a coupler, constructed and arranged to accept a gas line connection from a second compressor that is external to the portable oxygen generator and has a larger capacity than the first compressor; and a sensor that senses if the coupler is connected to the gas line connection and generates a signal such that, if the gas line connection is coupled to the coupler, the molecular sieves receive the flow of pressurized air from the second compressor and the first compressor is turned off.

2. The portable oxygen generator of claim 1, wherein the purge line couples output sides of the molecular sieves such that the purge gas comprises oxygen enriched gas.

3. The portable oxygen generator of claim 1, wherein the purge line valve is further operable to select among three pathways, wherein the three pathways include a balance pathway and at least two purge pathways having purge orifices, and wherein the at least two purge orifices correspond to the at least two purge pathways.

4. The portable oxygen generator of claim 1, wherein the purge line valve is operable to select between the at least two purge orifices in response to a flow rate of compressed air through the portable oxygen generator.

5. The portable oxygen generator of claim 1, wherein the purge line valve is operable to vary a duration of the purge cycle.

6. The portable oxygen generator of claim 5, wherein the purge line valve is operable to vary the duration of the purge cycle in response to a flow rate of compressed air through the oxygen generator.

7. The portable oxygen generator of claim 1, further comprising a secondary unit comprising:

a second compressor;

a control, configured and arranged to allow a user to select an output rate of the portable oxygen generator;

a power supply, configured and arranged to provide power to the second compressor; and a coupler, constructed and arranged to accept the gas line connection, wherein the secondary unit does not include any molecular sieve.

8. The portable oxygen generator of claim 1, further comprising a secondary unit comprising:

the second compressor arranged to provide a second flow of pressurized air, wherein the second compressor has a large capacity than the first compressor such that the second flow of pressurized air is greater than the flow of pressurized air provided by the first compressor, wherein the portable oxygen generator includes the at least two purge orifices, wherein the at least two purge orifices include a first purge orifice and a second purge orifice, wherein the first purge orifice has a first diameter, wherein the second purge orifice has a second diameter that is greater than the first diameter, wherein the controllable purse line valve is operable to select between the first purge orifice and the second purge orifice such that the first purge orifice is selected responsive to provision, by the first compressor, of the flow of pressurized air, and such that the second purge orifice is selected responsive to sensing, by the sensor, that the coupler is connected to the gasline connection from the second compressor.

9. A portable oxygen generator, comprising:

a first compressor, arranged to provide a flow of pressurized air;

a first molecular sieve, that receives the flow of pressurized air and produces a flow of oxygen enriched gas;

a second molecular sieve, that receives the flow of pressurized air and produces a flow of oxygen enriched gas;

a control valve that controls the flow of pressurized air such that it is selectively provided to the first and second molecular sieves;

a product container, that receives the flow of oxygen enriched gas;

an outlet valve, arranged to regulate an output flow of oxygen enriched gas to a user;

a purge line, in fluid communication with the first and second molecular sieves and that includes a controllable purge line valve that controls a flow of purge gas between the first and second molecular sieves during a purge cycle, the purge line coupling output sides of the molecular sieves such that the purge gas comprises oxygen enriched gas, wherein the controllable purge line valve is operable to select between more than two purge orifices having different diameters to control the amount of flow of the purge gas during the purge cycle; and a coupler, configured and arranged to accept a gas line connection from a second compressor that is external to the portable oxygen generator and has a larger capacity than the first compressor.

10. The portable oxygen generator of claim 9, wherein the purge line valve is further operable to select a balance pathway to divert a portion of the oxygen enriched gas from the first molecular sieve to the second molecular sieve.

11. The portable oxygen generator of claim 9, wherein the purge line valve is operable to select between more than two purge orifices in response to a flow rate of compressed air through the portable oxygen generator.

12. The portable oxygen generator of claim 9, wherein the purge line valve is operable to vary a duration of the purge cycle.

13. The portable oxygen generator of claim 12, wherein the purge line valve is operable to vary the duration of the purge cycle in response to a flow rate of compressed air through the portable oxygen generator.

14. A method for providing oxygen enriched gas to an end user at a range of flow rates, the method comprising:

compressing ambient air at a first flow rate using a first compressor;

controllably supplying the compressed air to molecular sieves;

storing oxygen enriched product gas from the molecular sieves;

controllably providing the oxygen enriched product gas to a user;

coupling a second compressor to the molecular sieves to supply compressed air to the molecular sieves at a second flow rate higher than the first flow rate;

periodically purging the molecular sieves by coupling the molecular sieves on an oxygen side thereof;

selecting, via a controllable purge line valve, between at least two purge orifices having different diameters in response to supplying of compressed air at a flow rate, wherein the flow rate is the first flow rate or the second flow rate; and in response to the coupling of the second compressor, turning off the first compressor.

15. A method as in claim 14, wherein selecting is performed between more than two purge orifices having different diameters in response to supplying of compressed air at a range of flow rates, wherein the range of flow rates includes the first flow rate and the second flow rate.

16. A method as in claim 15, further comprising varying a size of a purge orifice depending on a flow rate at which compressed air is supplied to the molecular sieves such that an amount of flow during a purge cycle is varied.

17. A method as in claim 14, further comprising:
    connecting a power supply of the first compressor to a power supply of the second compressor; and
    charging a battery of the power supply of the first compressor when the second compressor is coupled to the molecular sieves.

18. A method as in claim 14, further comprising varying a duration of a purge cycle of the molecular sieves depending on a flow rate at which compressed air is supplied to the molecular sieves.

19. A portable oxygen generator, comprising:
    a compressor, arranged to provide a flow of pressurized air;
    a first molecular sieve, in fluid communication with the compressor and that receives the flow of pressurized air and produces a flow of oxygen enriched gas;
    a second molecular sieve, in fluid communication with the compressor and that receives the flow of pressurized air and produces a flow of oxygen enriched gas;
    a control valve that controls the flow of pressurized air such that it is selectively provided to the first and second molecular sieves;
    a product container, coupled to the molecular sieves, that receives the flow of oxygen enriched gas;
    an outlet valve, arranged to regulate an output flow of oxygen enriched gas to a user from the product container;
    a purge line, in fluid communication with the first and second molecular sieves; and
    a controllable purge line valve that is configured and arranged to selectively control an amount of flow of purge gas during the purge cycle and is operable to select between at least two purge orifices having different diameters to control the amount of flow of purge gas during the purge cycle based on a flow rate of compressed air through the portable oxygen concentrator.

\* \* \* \* \*